United States Patent [19]

Fest et al.

[11] Patent Number: 4,726,834
[45] Date of Patent: * Feb. 23, 1988

[54] HERBICIDAL BENZODISULTAM DERIVATIVES, COMPOSITION, AND METHOD OF USE THEREFOR

[75] Inventors: Christa Fest, Wuppertal; Rolf Kirsten, Monheim; Joachim Kluth, Langenfeld; Klaus-Helmut Müller, Düsseldorf; Theodor Pfister, Monheim; Uwe Priesnitz, Solingen; Hans-Jochem Riebel, Wuppertal; Wolfgang Roy, Laggenfeld; Hans-Joachim Santel, Cologne; Robert R. Schmidt, Bergisch Gladbach, all of Fed. Rep. of Germany

[73] Assignee: Bayer Aktiengesellschaft, Leverkusen, Fed. Rep. of Germany

[ * ] Notice: The portion of the term of this patent subsequent to Jul. 14, 2004 has been disclaimed.

[21] Appl. No.: 889,985

[22] Filed: Jul. 24, 1986

[30] Foreign Application Priority Data

Aug. 6, 1985 [DE] Fed. Rep. of Germany ....... 3528099

[51] Int. Cl.$^4$ .................... A01N 43/62; C07D 243/04
[52] U.S. Cl. .......................................... 71/91; 540/552
[58] Field of Search ....................... 540/489, 490, 552; 71/91

[56] References Cited

PUBLICATIONS

Chem. Abstrs. vol. 87, No. 9, Aug. 29, 1977–"Condensation of Bis(chlorosulfonyl)methane with—Resulting Heterocycles"—Vincent Michel.

Primary Examiner—Henry R. Jiles
Assistant Examiner—J. G. Mullins

Attorney, Agent, or Firm—Sprung, Horn, Kramer & Woods

[57] ABSTRACT

Herbicidally active novel benzodisultams of the formula

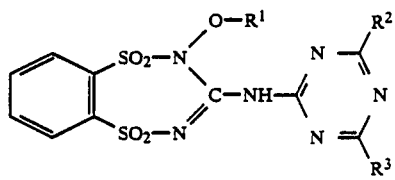

in which
  $R^1$ represents an optionally substituted radical from the series comprising alkyl, alkenyl, alkinyl, cycloalkyl, cycloalkylalkyl, aralkyl and aryl,
  $R^2$ represents hydrogen, fluorine, chlorine, bromine, hydroxyl, cyclopropyl, $C_1$–$C_4$-alkyl (which is optionally substituted by fluorine and/or chlorine), $C_1$–$C_4$-alkoxy [which is optionally substituted by fluorine and/or chlorine], $C_1$–$C_4$-alkylthio (which is optionally substituted by fluorine and/or chlorine), amino, or $C_1$–$C_4$-alkyl- or di-($C_1$–$C_4$-alkyl)-amino (which is optionally substituted by fluorine) and
  $R^3$ represents hydrogen, fluorine, chlorine, bromine, hydroxyl, cyclopropyl, $C_1$–$C_4$-alkyl (which is optionally substituted by fluorine and/or chlorine), $C_1$–$C_4$-alkoxy (which is optionally substituted by fluorine and/or chlorine), $C_1$–$C_4$-alkylthio (which is optionally substituted by fluorine and/or chlorine), amino or $C_1$–$C_4$-alkyl- or di-($C_1$–$C_4$-alkyl)-amino (which is optionally substituted by fluorine).

7 Claims, No Drawings

HERBICIDAL BENZODISULTAM DERIVATIVES, COMPOSITION, AND METHOD OF USE THEREFOR

The invention relates to novel benzodisultams which constitute a new class of substances, an inventive process for their preparation, and their use as herbicides.

Benzodisultams have not been disclosed in the literature to date. The use of similar compounds as herbicides is likewise unknown to date.

New benzodisultams of the general formula (I)

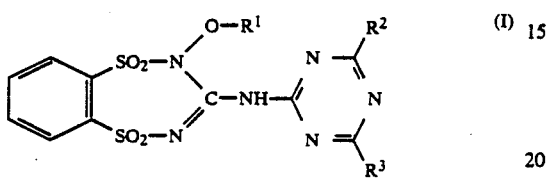

in which
  $R^1$ represents an optionally substituted radical from the series comprising alkyl, alkenyl, alkinyl, cycloalkyl, cycloalkylalkyl, aralkyl and aryl,
  $R^2$ represents hydrogen, fluorine, chlorine, bromine, hydroxyl, cyclopropyl, $C_1$–$C_4$-alkyl [which is optionally substituted by fluorine and/or chlorine], $C_1$–$C_4$-alkoxy [which is optionally substituted by fluorine and/or chlorine], $C_1$–$C_4$-alkylthio [which is optionally substituted by fluorine and/or chlorine], amino, or $C_1$–$C_4$-alkyl- or di-($C_1$–$C_4$-alkyl)-amino [which is optionally substituted by fluorine] and
  $R^3$ represents hydrogen, fluorine, chlorine, bromine, hydroxyl, cyclopropyl, $C_1$–$C_4$-alkyl [which is optionally substituted by fluorine and/or chlorine], $C_1$–$C_4$-alkoxy [which is optionally substituted by fluorine and/or chlorine], $C_1$–$C_4$-alkylthio [which is optionally substituted by fluorine and/or chlorine], amino or $C_1$–$C_4$-alkyl- or di-($C_1$–$C_4$-alkyl)-amino [which is optionally substituted by fluorine],
have now been found.

The new compounds of the formula (I) are obtained when benzene-1,2-disulphonyl dichloride of the formula (II)

is reacted with oxyguanidine derivatives of the formula (III)

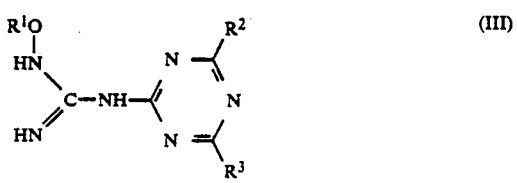

in which $R^1$, $R^2$ and $R^3$ have the meanings given above, in the presence of acid acceptors and, if appropriate, in the presence of diluents.

The new benzodisultams of the formula (I) are distinguished by a powerful herbicidal activity.

Surprisingly, the new compounds of the formula (I) have a substantially more powerful herbicidal action than many known chemical compounds having the same direction of action.

The present invention preferably relates to compounds of the formula (I) in which
  $R^1$ represents $C_1$–$C_{12}$-alkyl [which is optionally substituted by fluorine, chlorine, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl-carbonyl, $C_1$–$C_4$-alkoxy-carbonyl, $C_1$–$C_4$-alkylamino-carbonyl or di-($C_1$–$C_4$-alkyl)-amino-carbonyl], $C_3$–$C_6$-alkenyl [which is optionally substituted by fluorine, chlorine or bromine], $C_3$–$C_6$-alkinyl, $C_3$–$C_6$-cycloalkyl, $C_3$–$C_6$-cycloalkyl-$C_1$- or $C_2$-alkyl, phenyl-$C_1$- or $C_2$-alkyl [which is optionally substituted by fluorine, chlorine, nitro, cyano, $C_1$–$C_4$-alkyl, $C_1$–$C_4$-alkoxy or $C_1$–$C_4$-alkoxy-carbonyl] or phenyl [which is optionally substituted by fluorine, chlorine, nitro, cyano, $C_1$–$C_4$-alkyl, trifluoromethyl, $C_1$–$C_4$-alkoxy, $C_1$- or $C_2$-fluoroalkoxy, $C_1$–$C_4$-alkylthio, trifluoromethylthio or $C_1$–$C_4$-alkoxy-carbonyl],
and in which furthermore
  $R^2$ represents hydrogen, fluorine, chlorine, hydroxyl, cyclopropyl, methyl [which is optionally substituted by fluorine and/or chlorine], $C_1$–$C_3$-alkoxy [which is optionally substituted by fluorine and/or chlorine], $C_1$–$C_3$-alkylthio [which is optionally substituted by fluorine and/or chlorine], amino, $C_1$–$C_3$-alkyl- or di-($C_1$–$C_3$-alkyl)-amino [which is optionally substituted by fluorine] and
  $R^3$ represents hydrogen, fluorine, chlorine, hydroxyl, cyclopropyl, methyl [which is optionally substituted by fluorine and/or chlorine], $C_1$–$C_3$-alkoxy [which is optionally substituted by fluorine and/or chlorine], $C_1$–$C_3$-alkylthio [which is optionally substituted by fluorine and/or chlorine] amino, or $C_1$–$C_3$-alkyl or di-($C_1$–$C_3$-alkyl)amino [which is optionally substituted by fluorine].

The invention relates in particular to compounds of the formula (I) in which
  $R^1$ represents $C_1$–$C_8$-alkyl [which is optionally substituted by fluorine or chlorine], $C_3$- or $C_4$-alkenyl, $C_1$- or $C_2$-alkoxy-carbonylmethyl, phenyl, phenylethyl or benzyl [which is optionally substituted by fluorine, chlorine, nitro, cyano, methyl, methoxy or methoxy-carbonyl],
  $R^2$ represents hydrogen, chlorine, methyl, methoxy, ethoxy, mthylthio, ethylthio, methylamino, ethylamino, dimethylamino or diethylamino and
  $R^3$ represents hydrogen, chloride, methyl, methoxy, ethoxy, methylthio, ethylthio, methylamino, ethylamino, dimethylamino or diethylamino.

If, for example, N'-(4,6-dimethyl-1,3,5-triazin-2-yl)-N''-allyloxy-guanidine and benzene-1,2-disulphonyl dichloride are used as starting materials in the process according to the invention, the course of the reaction can be represented by the following equation:

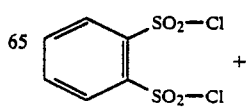

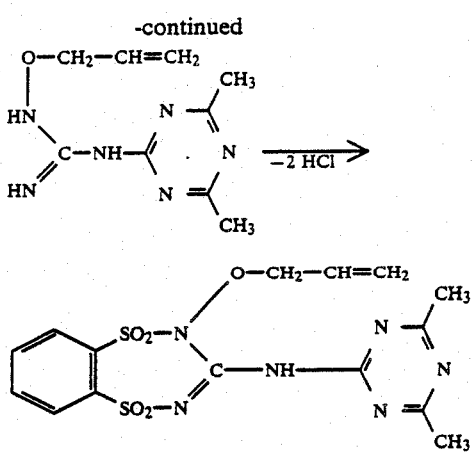

Benzene-1,2-disulphonyl dichloride of the formula (II) which is to be used as a starting material in the process according to the invention is already known (see J. Org. Chem. 31 (1966), 3289–3292).

Formula (III) gives a general definition of the oxyguanidine derivatives furthermore to be used as starting materials in the process according to the invention. In formula (III), $R^1$, $R^2$ and $R^3$ have the same preferred or particular meanings as stated above in connection with the definition of substituents for formula (I) as being preferred or particularly preferred.

The following may be mentioned as examples of starting materials of the formula (III): N'-(4,6-dimethyl-s-triazin-2-yl)-, N'-(4-methoxy-6-methyl-s-triazin-2-yl)-, N'-(4-ethoxy-6-methyl-s-triazin-2-yl)-, N'-(4,6-dimethoxy-s-triazin-2-yl)-, N'-(4,6-diethoxy-s-triazin-2-yl)-, N'-(4-ethoxy-6-methoxy-s-triazin-2-yl)-, N'-(4-methyl-6-methylthio-s-triazin-2-yl)-, N'-(4-ethylthio-6-methyl-s-triazin-2-yl)-, N'-(4-methoxy-6-methylthio-s-triazin-2-yl)-, N'-(4-ethoxy-6-methylthio-s-triazin-2-yl)-, N'-(4-ethylthio-6-methoxy-s-triazin-2-yl)-, N'-(4-ethoxy-6-ethylthio-s-triazin-2-yl)-, N'-(4,6-bis-methylthio-s-triazin-2-yl)-, N'-4,6-(bis-ethylthio-s-triazin-2-yl)-, N'-(4-methyl-6-methylamino-s-triazin-2-yl)-, N'-(4-ethylamino-6-methyl-s-triazin-2-yl)-, N'-(4-dimethylamino-6-methyl-s-triazin-2-yl)-, N'-(4-diethylamino-6-methyl-s-triazin-2-yl)-, N'-(4-methoxy-6-methylamino-s-triazin-2-yl)-, N'-(4-ethylamino-6-methoxy-s-triazin-2-yl)-, N'-(4-dimethylamino-6-methoxy-s-triazin-2-yl)-, N'-(4-diethylamino-6-methoxy-s-triazin-2-yl)-, N'-(4-ethoxy-6-methylamino-s-triazin-2-yl)-, N'-(4-ethoxy-6-ethylamino-s-triazin-2-yl)-, N'-(4-dimethylamino-6-ethoxy-s-triazin-2-yl)-, N'-(4-diethylamino-6-ethoxy-s-triazin-2-yl)-, N'-(4-methylamino-6-methylthio-s-triazin-2-yl)-, N'-(4-ethylamino-6-methylthio-s-triazin-2-yl)-, N'-(4-dimethylamino-6-methylthio-s-triazin-2-yl)-, N'-(4-diethylamino-6-methylthio-s-triazin-2-yl)-, N'-(4-ethylthio-6-methylamino-s-triazin-2-yl)-, N'-(4-dimethylamino-6-ethylthio-s-triazin-2-yl)- and N'-(4-diethylamino-6-ethylthio-s-triazin-2-yl)-N''-methoxy-guanidine, -N''-ethoxy-guanidine, -N''-propoxyguanidine, -N''-iso-propoxy-guanidine, -N''-butoxy-guanidine, -N''-isobutoxy-guanidine, -N''-sec.-butoxy-guanidine, -N''-pentoxy-guanidine, -N''-isopentoxy-guanidine, -N''-hexyloxyguanidine, -N''-octyloxy-guanidine, -N''-allyloxy-guanidine, -N''-(2-chloro-ethoxy)-guanidine, -N''-(2-fluoro-ethoxy)-guanidine, -N''-(2-chloro-propoxy)-guanidine, -N''-(2-fluoropropoxy)-guanidine, -N''-(3-chloro-propoxy)-guanidine, -N''-(4-chloro-butoxy)-guanidine, -N'''-methoxycarbonylmethoxyguanidine, -N''-ethoxycarbonylmethoxy-guanidine, -N''-(1-methoxy-carbonylethoxy)-guanidine, -N''-(1-ethoxy-carbonylethoxy)-guanidine, -N''-dimethylamino-carbonylmethoxy-guanidine, -N''-(2-phenyl-ethoxy)-guanidine, -N''-phenoxy-guanidine, -N''-(4-methylbenzyloxy)-guanidine, -N''-(4-fluorobenzyloxy)-guanidine, -N''-(4-chloro-benzyloxy)-guanidine, -N''-(4-nitro-benzyloxy)-guanidine, -N''-(2,6-dichloro-benzyloxy)-guanidine, -N''-(4-methoxycarbonylbenzyloxy)-guanidine and -N''-(4-ethoxycarbonyl-benzyloxy)guanidine.

Some of the starting materials of the formula (III) are known (see EP-A No. 121 082).

The compounds of the formula (III) are obtained when cyanoaminotriazine derivatives of the formula (IV)

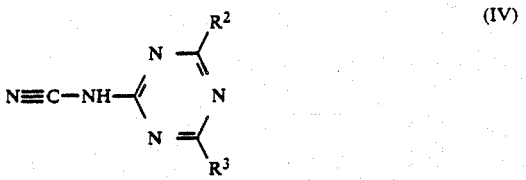

in which $R^2$ and $R^3$ have the meanings given above, are reacted with hydroxylamine derivatives of the formula (V)

in which $R^1$ has the meaning given above, or their hydrochlorides, if appropriate in the presence of diluents, such as, for example, ethanol, propanol or butanol, at temperatures between −20° C. and 150° C., and, if appropriate, the reaction products are treated with acid acceptors, such as, for example, ammonia, potassium carbonate or sodium hydroxide.

The cyanoaminotriazine derivatives of the formula (IV) are known (see DE-OS (German Published Specification) No. 3,334,455).

The compounds of the formula (IV) are essentially obtained by the following synthesis routes: (a¹) by reactions of alkali metal or alkaline earth metal salts of cyanamide—such as, for example, sodium cyanamide or calcium cyanamide—with chlorotriazines of the formula (VI)

in which $R^2$ and $R^3$ have the meanings given above, if appropriate in the presence of acid acceptors and, if appropriate, in the presence of diluents, such as, for example, ethanol, acetone, acetonitrile, dimethylformamide, dimethyl sulphoxide or water, at temperatures between −10° C. and 100° C. After the solution has been evaporated down and the residue dissolved in water, the cyanoaminotriazine derivatives of the formula (IV) can be precipitated by acidification, for example with hydrochloric acid, and isolated by filtration under suction.

The chlorotriazines of the formula (VI) to be used as starting materials for the process, described above under (a¹), for the preparation of the cyanoaminotriazine derivatives of the formula (IV) are known and/or can be prepared by processes which are in themselves known (see U.S. Pat. No. 3,154,547 and U.S. Pat. No. 4,160,037).

In another process, cyanoaminotriazine derivatives of the formula (IV) are obtained if (a²) dichlorotriazines of the formula (VIa)

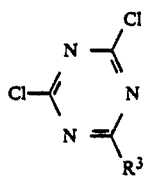
(VIa)

in which $R^3$ has the meaning given above, are reacted with alkali metal salts or alkaline earth metal salts of cyanamide, such as, for example, with disodium cyanamide, in the presence of a diluent, such as, for example, water, at temperatures between $-10°$ C. and $+50°$ C., and the resulting metal salt of the monochlorocyanoaminotriazine of the formula (IVa)

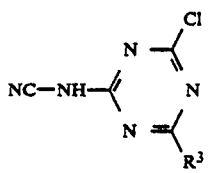
(IVa)

in which $R^3$ has the meaning given above, is converted to the ree monochloro-cyanoaminotriazine of the formula (IVa) with an acid, such as, for example, hydrochloric acid.

The monochloro-cyanoaminotriazines of the formula (IVa) can be reacted with alcohols or alkanethiols or with alkali metal salts of these compounds or with monoalkyl- or dialkylamines to prepare the corresponding cyanoaminotriazines of the formula (IV), in which $R^2$ represents alkoxy, alkylthio, alkylamino or dialkylamino.

The hydroxylamine derivatives of the formula (V) which are furthermore to be used as starting materials are likewise known and can be prepared by processes which are in themselves known (see Chem. Pharm. Bull. 15 (1967), 345; Bull. Soc. Chim. France 1958, 664; Synthesis 1976, 682; J. Chem. Soc. 1930, 228 and Helv. Chim. Acta 45 (1962), (1387).

The process, according to the invention, for the preparation of the new compounds of the formula (I) is preferably carried out using diluents. Suitable diluents are virtually all inert organic solvents, preferably aprotic polar solvents. These include optionally halogenated hydrocarbons, such as, for example, methylene chloride, chloroform, toluene and chlorobenzene, nitriles, such as, for example, acetonitrile and propionitrile, dimethylformamide, dimethylacetamide, dimethyl sulphoxide, sulpholane, hexamethylphosphoric acid triamide, 1,2-dimethoxyethane, pyridine and 2-methyl-5-ethyl-pyridine.

Virtually all customarily used acid-binding agents can be employed as acid acceptors in the process according to the invention. These include in particular alkali metal and alkaline earth metal hydrides, organometallic compounds, such as butyl-lithium, and aliphatic, aromatic or heterocyclic amines, such as trimethylamine, triethylamine, N,N-dimethylaniline, N,N-dimethyl-benzylamine, diazabicyclooctane (DABCO), diazabicycloundecene (DBU), pyridine, 2-methyl-5-ethyl-pyridine and 4-dimethylaminopyridine.

In the process according to the invention, the reaction temperatures can be varied within a relatively wide range. In general, the reaction is carried out at between $-80°$ C. and $+100°$ C., preferably between $-40°$ C. and $+50°$ C. The process according to the invention is carried out in general under atmospheric pressure.

To carry out the process according to the invention, in general between 1.0 and 1.5 mols, preferably between 1.0 and 1.2 mols, of benzene-1,2-disulphonyl dichloride of the formula (II) are employed per mol of oxyguanidine derivative of the formula (III). The reaction components are usually combined at room temperature or with external cooling, and the reaction mixture is stirred until the reaction is complete.

Working up and isolation of the new compounds of the formula (I) can be carried out by customary methods. For example, the reaction mixture—if appropriate after dilution with a solvent which is virtually immiscible with water, such as, for example methylene chloride—is washed with dilute hydrochloric acid and with water, dried, filtered and evaporated down. The product of the formula (I) which remains in the residue is crystallized by trituration with a suitable organic solvent such as, for example, ethanol, and isolated by filtration under suction.

The active compounds according to the invention influence plant growth and can therefore be used as defoliants, desiccants, agents for destroying broad-leaved plants and germination inhibitors, and especially as weedkillers. By weeds, in the broadest sense, there are to be understood all plants which grow in locations where they are undesired. Whether the substances according to the invention act as total or selective herbicides depending essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is, liquid solvents and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl napthalenes, chlorinated aromatics or chlorinated aliphatic hydrocarbons such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixtures being possible.

Herbicides which are suitable for the mixtures are known herbicides, such as, for example, N-(2-benzothiazolyl)-N,N'-dimethylurea, 3-(3-chloro-4-methylphenyl)-1,1-dimethylurea, 3-(4-disopropylphenyl)-1,1-dimethylurea, 4-amino-6-(1,1-dimethylethyl)-3-methylthio-1,2,4-triazin-5-(4H)-one, 4-amino-6-(1,1-dimethyl-ethery)-3-ethylthio-1,2,4-triazin-5-(4H)-one, 1-amino-6-ethylthio-3-(2,2-dimethylpropyl)-1,3,5-triazine-2,4-(1H,3H)-dione, 4-amino-3-methyl-6-phenyl-1,2,4-triazin-5-(4H)-one, 2-chloro-4-ethylamino-6-isopropylamino-1,3,5-triazine, the R-enantiomer of (trimethylsilyl)-methyl 2-[4-(3,5-dichloro-pyrid-2-yloxy)-phenoxy]-propionate, the R-enantiomer of (2-benzyloxy)-ethyl 2-[4-(3,5-dichloropyrid-2-yloxy)-phenoxy]propionate, 2,4-dichlorophenoxyacetic acid, 2-(2,4-dichlorophenoxy)-propionic acid, 4-chloro-2-methylphenoxyacetic acid, 2-(2-methyl-4-chloro-phenoxy)-propionic acid, 3,5-diiodo-4-hydroxybenzonitrile, 3,5-dibromo-4-hydroxybenzonitrile and diphenyl ether and phenylpyridazines, such as, for example, pyridates, Surprisingly, some mixtures also exhibit a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.01 and 10 kg of active compound per hectare of soil area, preferably between 0.05 and 5 kg per ha.

The preparation and the use of the active compounds according to the invention are described in the examples below.

PREPARATION EXAMPLES

EXAMPLE 1

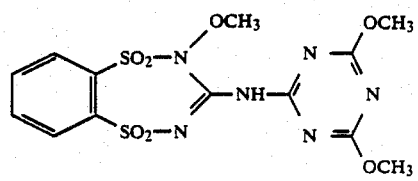

7.1 g (0.025 mol) of benzene-1,2-disulphonyl chloride are added in portions to a mixture of 5.6 g (0.025 mol) of N'-(4,6-dimethoxy-1,3,5-triazin-2-yl)-N''-methoxy-guanidine, 6 g (0.025 mol) of DABCO and 60 ml of methylene chloride at −10° C. Stirring is carried out for 15 hours at 0° to −5° C. The reaction mixture is then washed with ice-cooled dilute hydrochloric acid and ice water. The methylene chloride solution is dried and evaporated down.

After incipient distillation has been carried out, 4.6 g (43% of theory) of the compound of the structural formula given above are obtained in the form of an amorphous mass.

The substance is characterized by the $H^1$-NMR spectrum.

The compounds of the formula (I) which are listed in Table 1 below can be prepared by the process described by way of example in the example above:

TABLE 1

(I) [structure shown: benzene ring fused with a ring containing two $SO_2-N$ groups, with $O-R^1$ and $C-NH-$ substituents, connected to a 1,3,5-triazine ring bearing $R^2$ and $R^3$ substituents]

| Example No. | $R^1$ | $R^2$ | $R^3$ | Melting point [°C] |
|---|---|---|---|---|
| 2 | —$C_2H_5$ | —$OCH_3$ | —$OCH_3$ | |
| 3 | —$CH_2$—CH=$CH_2$ | —$OCH_3$ | —$OCH_3$ | |
| 4 | —$CH_3$ | —$OCH_3$ | —$OC_2H_5$ | |
| 5 | —$C_4H_9$—n | —$OCH_3$ | —$OC_2H_5$ | |
| 6 | —$CH_3$ | —$OCH_3$ | —$N(C_2H_5)_2$ | |
| 7 | —$C_3H_7$—n | —$SCH_3$ | —$NHC_2H_5$ | |
| 8 | —$CH_3$ | —$CH_3$ | —$OCH_3$ | amorphous |
| 9 | —$C_8H_{17}$—n | —$CH_3$ | —$OCH_3$ | |
| 10 | —$CH_2$—(phenyl) | —$CH_3$ | —$OCH_3$ | |
| 11 | —$CH_3$ | —$OCH_3$ | —$SCH_3$ | |
| 12 | —$CH_3$ | —$CH_3$ | —$OC_2H_5$ | |
| 13 | —$CH_2$—(phenyl) | —$CH_3$ | —$OC_2H_5$ | amorphous |
| 14 | —$CH_3$ | —$SCH_3$ | —$NHC_2H_5$ | |
| 15 | —$CH_3$ | —$C_2H_5$ | —$OCH_3$ | |
| 16 | —$CH_3$ | —$CH_3$ | —$CH_3$ | amorphous |
| 17 | —$CH_2$—CH=$CH_2$ | —$CH_3$ | —$CH_3$ | |
| 18 | —$CH_2$—(phenyl-$COOC_2H_5$) | —$CH_3$ | —$CH_3$ | 195 |
| 19 | —$CH(CH_3)_2$ | —$CH_3$ | —$OCH_3$ | amorphous |
| 20 | —$CH(CH_3)_2$ | —$CH_3$ | —$OC_2H_5$ | amorphous |
| 21 | —$(CH_2)_7$—$CH_3$ | —$OCH_3$ | —$OCH_3$ | 110 |
| 22 | —$CH_2$—(phenyl) | —$OCH_3$ | —$OCH_3$ | 185 |
| 23 | —$CH_2$—(2,6-dichlorophenyl) | —$CH_3$ | —$CH_3$ | 150 |

PREPARATION OF STARTING COMPOUNDS OF THE FORMULA (III) EXAMPLE (III-1)

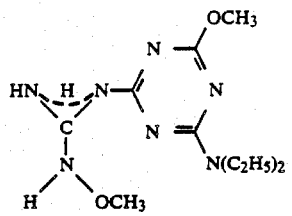

A mixture of 66.5 g (0.3 mol) of 2-cyanoamino-4-diethylamino-6-methoxy-s-triazine, 50 g (0.8 mol) of O-methylhydroxylamine hydrochloride and 300 ml of ethanol is heated at the boil under reflux for 15 hours. Thereafter, the mixture is filtered, the filtrate is evaporated down, the residue is taken up in about 200 ml of water, the solution is rendered alkaline with sodium hydroxide solution, and the product obtained in crystalline form during this procedure is isolated by filtration under suction.

35.0 g (43% of theory) or N'-(4-diethylamino-6-methoxy-s-triazin-2-yl)-N''-methoxy-guanidine of melting point 112° C. are obtained.

The compounds of the formula (III) which are listed in Table 2 below can be prepared analogously:

TABLE 2

| Example No. | $R^1$ | $R^2$ | $R^3$ | Melting point [°C.] |
|---|---|---|---|---|
| III-2 | —$CH_3$ | —$SCH_3$ | —$NHC_2H_5$ | 117 |
| III-3 | —$CH_3$ | —$SCH_3$ | —$NHCH_3$ | |
| III-4 | —$CH_3$ | —Cl | —$N(C_2H_5)_2$ | |
| III-5 | —$C_2H_5$ | —$OCH_3$ | —$N(C_2H_5)_2$ | |
| III-6 | —$C_3H_7$—n | —$SCH_3$ | —$NHC_2H_5$ | |
| III-7 | —$CH(CH_3)_2$ | —$OCH_3$ | —$NHCH_3$ | |
| III-8 | —$CH_2$—$CH$=$CH_2$ | —$OCH_3$ | —$N(CH_3)_2$ | |
| III-9 | —$C_4H_9$—n | —$OCH_3$ | —$N(CH_3)_2$ | |
| III-10 | —$CH_2$—C$_6$H$_5$ | —$OCH_3$ | —$N(CH_3)_2$ | |
| III-11 | —$CH_2COOC_2H_5$ | —$OCH_3$ | —$N(CH_3)_2$ | |
| III-12 | —$CH_2$—C$_6$H$_4$—$CH_3$ | —$OCH_3$ | —$N(CH_3)_2$ | |
| III-13 | —$CH_3$ | —$CH_3$ | —$OCH_3$ | 126 |
| III-14 | —$CH_2$—C$_6$H$_5$ | —$CH_3$ | —$OCH_3$ | 112 |
| III-15 | —$C_8H_{17}$ | —$CH_3$ | —$OCH_3$ | 95 |
| III-16 | —$CH_2$—C$_6$H$_5$ | —$SCH_3$ | —$NHC_2H_5$ | 122 |
| III-17 | —$CH_3$ | —$CH_3$ | —$OC_2H_5$ | 107 |
| III-18 | —$CH_2$—C$_6$H$_5$ | —$CH_3$ | —$OC_2H_5$ | $n_D^{21}$ = 1.5824 |
| III-19 | —$CH_3$ | —$CH_3$ | —$CH_3$ | 112 |

TABLE 2-continued $$\text{(III)}$$

Structure (III): HN(OR¹)–C(=NH)–NH–C(=N–)–N=C(R²)–N=C(R³)– (triazine with OR¹-aminoguanidine substituent)

| Example No. | R¹ | R² | R³ | Melting point [°C.] |
|---|---|---|---|---|
| III-20 | —CH₂—C₆H₅ | —CH₃ | —CH₃ |  |
| III-21 | —CH₂—CH=CH₂ | —CH₃ | —CH₃ |  |
| III-22 | —CH₃ | —OCH₃ | —OCH₃ | 107 |
| III-23 | —CH₂—C₆H₅ | —OCH₃ | —OCH₃ | 127 |
| III-24 | —CH₂—C(CH₃)₃ | —CH₃ | —CH₃ |  |
| III-25 | —CH₂CH₂—OCH₃ | —OCH₃ | —OCH₃ |  |
| III-26 | —CH₂CH₂—OC₂H₅ | —CH₃ | —OCH₃ |  |
| III-27 | —CH₂CH₂—SCH₃ | —CH₃ | —OC₂H₅ |  |
| III-28 | —CH₂CH₂—SC₂H₅ | —CH₃ | —CH₃ |  |
| III-29 | —CH₂—CONH₂ | —OCH₃ | —OCH₃ |  |
| III-30 | —CH₂—CH=CHCl | —CH₃ | —OCH₃ |  |
| III-30 | —CH(C₆H₅)₂ | —CH₃ | —CH₃ |  |
| III-32 | —C(C₆H₅)₃ | —CH₃ | —CH₃ |  |
| III-33 | —CH₃ | —C₂H₅ | —OCH₃ |  |
| III-34 | —CH₃ | —SCH₃ | —OCH₃ |  |
| III-35 | —CH₃ | —OC₂H₅ | —OCH₃ |  |
| III-36 | —CH₃ | —NH—C₂H₅ | —OCH₃ |  |
| III-37 | —CH₃ | —N(CH₃)₂ | —OCH₃ |  |
| III-38 | —CH₃ | —CH₃ | —SCH₃ |  |
| III-39 | —CH₃ | —NH—CH₃ | —CH₃ | 128 |
| III-40 | —CH₃ | —N(CH₃)₂ | —CH₃ | 113 |
| III-41 | —C₃H₇—i | —OCH₃ | —OCH₃ |  |
| III-42 | —C₈H₁₇—n | —OCH₃ | —OCH₃ | 98 |
| III-43 | —CH₃ | —OCH₃ | —NHCH₃ | 176 |
| III-44 | —CH₃ | —OC₂H₅ | —NHCH₃ | 159 |
| III-45 | —C₃H₇—i | —OC₂H₅ | —NHCH₃ | 152 |
| III-46 | —CH₂—C₆H₅ | —OC₂H₅ | —NHCH₃ | 158 |
| III-47 | —CH(CH₃)₂ | —CH₃ | —OCH₃ | amorphous |
| III-48 | —CH₂CH(CH₃)₂ | —CH₃ | —OCH₃ | amorphous |
| III-49 | —CH(CH₃)₂ | —CH₃ | —OC₂H₅ | amorphous |
| III-50 | —CH₂CH(CH₃)₂ | —CH₃ | —OC₂H₅ | amorphous |
| III-51 | —CH(CH₃)₂ | —CH₃ | —N(CH₃)₂ | 100 |
| III-52 | —CH₂CH(CH₃)₂ | —CH₃ | —N(CH₃)₂ | amorphous |
| III-53 | —CH(CH₃)₂ | —CH₃ | —NHCH₃ | 127 |
| III-54 | —CH₂CH(CH₃)₂ | —CH₃ | —NHCH₃ | 133 |
| III-55 | —CH₃ | —NHCH₃ | —NHCH₃ | 204 |
| III-56 | —CH(CH₃)₂ | —SCH₃ | —NHC₂H₅ | amorphous |

TABLE 2-continued (III)

| Example No. | R¹ | R² | R³ | Melting point [°C.] |
|---|---|---|---|---|
| III-57 | $-CH_2-\phenyl-COOC_2H_5$ | $-CH_3$ | $-CH_3$ | 133 |

PREPARATION OF STARTING MATERIALS OF THE FORMULA (IV)

EXAMPLE (IV-1)

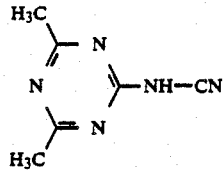

(Process (a¹))

A solution of 18.0 g (0.21 mol) of the disodium salt of cyanamide in 100 ml of water are added dropwise in the course of 4 hours to a suspension of 28.7 g (0.2 mol) of 2-chloro-4,6-dimethyl-1,3,5-triazine in 100 ml of ice water at a temperature of 0° C. to 5° C., while stirring vigorously. Thereafter, stirring is continued at 20° C., and the mixture is left to stand for 15 to 16 hours. After the mixture has been acidified to pH 2 with concentrated hydrochloric acid, the product is filtered off under suction, washed four times with 20 ml of ice water and dried.

19.7 g (66% of theory) of 2-cyanoamino-4,6-dimethyl-1,3,5-triazine of melting point 241° C. (decomposition) are obtained.

EXAMPLE (IV-2)

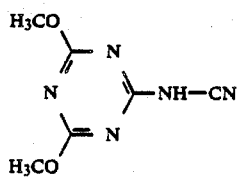

(Process a²))

A solution of 1.6 g (0.069 mol) of sodium in 20 ml of methanol is added dropwise to a suspension of 6 g (0.032 mol) of 4-chloro-2-cyanoamino-6-methoxy-1,3,5-triazine in 50 ml of methanol at 20° C. to 30° C. Stirring is then continued for 15 hours at 20° C. The solvent is distilled off, the residue is dissolved in 30 ml of water and the solution is acidified with hydrochloric acid. The crystals formed are filtered off under suction and dried.

5.9 g (92% of theory) of 2-cyanoamino-4,6-dimethoxy-1,3,5-triazine are obtained. The product is characterized by ¹H-NMR spectra.

The following compounds of the formula (IV) can be prepared analogously to Example (IV-1) and (IV-2):

TABLE 3

(IV)

| Example No. | R² | R³ | Melting point [°C.] |
|---|---|---|---|
| IV-3 | OCH₃ | N(C₂H₅)₂ | 114 |
| IV-4 | SCH₃ | NHC₂H₅ | |
| IV-5 | OCH₃ | NHCH₃ | 210 |
| IV-6 | OC₂H₅ | OC₂H₅ | |
| IV-7 | OCH₃ | CH₃ | 184 |
| IV-8 | OCH(CH₃)₂ | CH₃ | |
| IV-9 | SCH₃ | CH₃ | |
| IV-10 | SC₂H₅ | CH₃ | |
| IV-11 | SCH(CH₃)₂ | CH₃ | |
| IV-12 | NHCH₃ | CH₃ | |
| IV-13 | NHCH(CH₃)₂ | CH₃ | |
| IV-14 | N(CH₃)₂ | CH₃ | 267 |
| IV-15 | OC₂H₅ | CH₃ | 195 (decomposition) |
| IV-16 | C₂H₅ | OCH₃ | |
| IV-17 | SCH₃ | OCH₃ | |
| IV-18 | OC₂H₅ | OCH₃ | |
| IV-19 | OCH₃ | NHCH₃ | |
| IV-20 | OCH₃ | N(CH₃)₂ | >260 |
| IV-21 | N(CH₃)₂ | N(CH₃)₂ | >260 |
| IV-22 | NHC₃H₇ | NHC₃H₇ | 264 |
| IV-23 | NHCH(CH₃)₂ | NHCH(CH₃)₂ | 259 |
| IV-24 | NHC₂H₅ | NHC₂H₅ | 248 |
| IV-25 | OCH₃ | NHC₂H₅ | 266 |
| IV-26 | OCH₃ | NHCH(CH₃)₂ | 193 |
| IV-27 | NHC₄H₉ | NHC₄H₉ | 260 |
| IV-28 | SCH₃ | SCH₃ | 206 |
| IV-29 | OC₂H₅ | NHCH₃ | 227 |
| IV-30 | NHCH₃ | NHCH₃ | >260 |
| IV-31 | OC₂H₅ | NHC₂H₅ | 184 |
| IV-32 | NH₂ | CH₃ | >260 |
| IV-33 | NHCH₃ | CH₃ | 276 |
| IV-34 | NHC₂H₅ | CH₃ | 238 |

PREPARATION OF STARTING MATERIALS OF THE FORMULA (IVa)

EXAMPLE (IVa-1)

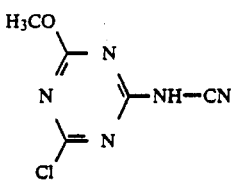

A solution of 9 g (0.043 mol) of the sodium salt of 4-chloro-2-cyanoamino-6-methoxy-1,3,5-triazine in 90 ml of water is acidified with hydrochloric acid, and the crystals formed are then filtered off under suction.

6.7 g (84% of theory) of 4-chloro-2-cyanoamino-6-methoxy-1,3,5-triazine of melting point >260° C. are obtained. The product is characterized by $^1$H-NMR spectra.

The following compounds of the formula (IVa) can be prepared analogously to Example (IVa-1):

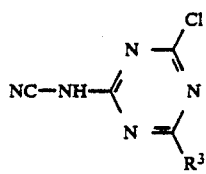

(IVa)

TABLE 4

| Example No. | $R^3$ | Melting point (°C.) |
| --- | --- | --- |
| IVa-2 | $CH_3$ | 250 (decomposition) |
| IVa-3 | Cl | >250 |
| IVa-4 | $N(C_2H_5)_2$ | 156 |
| IVa-5 | $NHCH_3$ | >260 |
| IVa-6 | $NHC_4H_9$ | 158 |
| IVa-7 | $NHC_3H_7$ | 136 |
| IVa-8 | $NHCH(CH_3)_2$ | 167 |
| IVa-9 | $NHC_2H_5$ | 153 |
| IVa-10 | $N(CH_3)_2$ | 222 |

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated contriol. The figures denote:

0% = no action (like untreated control)
100% = total destruction

In this test, the active compound according to preparative Example 1 exhibits a very good herbicidal activity and can be applied for the selective control of mono- and dicotyledoneous weeds in wheat.

EXAMPLE B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, the active compound according to preparative Example 1 exhibits a very good herbicidal activity and can be applied for the selective control of mono- and dicotyledoneous weeds in wheat and barley.

It will be understood that the specification and examples are illustrative but not limitative of the present invention and that other embodiments within the spirit and scope of the invention will suggest themselves to those skilled in the art.

We claim:

1. A benzodisultam of the formula

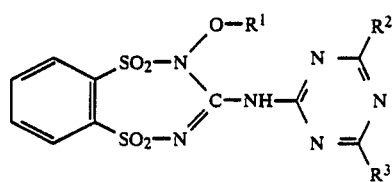

in which $R^1$ represents $C_1$-$C_{12}$-alkyl (which is optionally substituted by fluorine, chlorine, cyano, $C_1$-$C_4$-alkoxy, $C_1$-$C_4$-alkylthio, $C_1$-$C_4$-alkylsulphinyl, $C_1$-$C_4$-alkylsulphonyl, $C_1$-$C_4$-alkyl-carbonyl, $C_1$-$C_4$-alkoxy-carbonyl, $C_1$-$C_4$-alkylamino-carbonyl or di-($C_1$-$C_4$-alkyl)-aminocarbonyl), $C_3$-$C_6$-alkenyl (which is optionally substituted by fluorine, chlorine or bromine), $C_3$-$C_6$-alkinyl, $C_3$-$C_6$-cycloalkyl, $C_3$-$C_6$-cycloalkyl-$C_1$- or $C_2$-alkyl, phenyl-$C_1$- or $C_2$-alkyl (which is optionally substituted by fluorine, chlorine, nitro, cyano, $C_1$-$C_4$-alkyl, $C_1$-$C_4$-alkoxy or $C_1$-$C_4$-alkoxy-carbonyl) or phenyl (which is optionally substituted by fluorine, chlorine, nitro, cyano, $C_1$-$C_4$-alkyl, trifluoromethyl, $C_1$-$C_4$-alkoxy, $C_1$- or $C_2$-fluoroalkoxy, $C_1$-$C_4$-alkylthio, trifluoromethylthio or $C_1$-$C_4$-alkoxy-carbonyl), $R^2$ represents hydrogen, fluorine, chlorine, hydroxyl, cyclopropyl, methyl (which is optionally substituted by fluorine and/or chlorine), $C_1$-$C_3$-alkoxy (which is optionally substituted by fluorine and/or chlorine), $C_1$-$C_3$-alkylthio (which is optionally substituted by fluorine and/or chlorine), amino, $C_1$-$C_3$-alkyl- or di-($C_1$-$C_3$-alkyl)-amino (which is optionally substituted by fluorine) and $R^3$ represents hydrogen, fluorine, chlorine, hydroxyl, cyclopropyl, methyl (which is optionally substituted by fluorine and/or chlorine), $C_1$-$C_3$-alkoxy (which is optionally substituted by fluorine and/or chlorine), $C_1$-$C_3$-alkylthio (which is optionally substituted by fluorine and/or chlorine) amino, or $C_1$-$C_3$-alkyl or di-($C_1$-$C_3$-alkyl)amino (which is optionally substituted by fluorine).

2. A benzodisultam according to claim 1, in which
$R^1$ represents $C_1$-$C_8$-alkyl (which is optionally substituted by fluorine or chlorine), $C_3$- or $C_4$-alkenyl, $C_1$- or $C_2$-alkoxy-carbonylmethyl, phenyl, phenylethyl or benzyl (which is optionally substituted by fluorine, chlorine, nitro, cyano, methyl, methoxy or methoxy-carbonyl),
$R^2$ represents hydrogen, chlorine, methyl, methoxy, ethoxy, methylthio, ethylthio, methylamino, ethylamino, dimethylamino or diethylamino and
$R^3$ represents hydrogen, chlorine, methyl, methoxy, ethoxy, methylthio, ethylthio, methylamino, ethylamino, dimethylamino or diethylamino.

3. A benzodisultam according to claim 1, of the formula

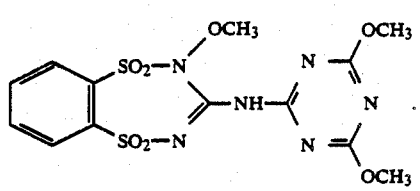

4. A benzodisultam according to claim 1, of the formula

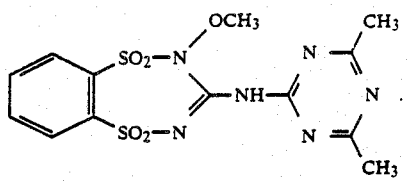

5. A herbicidal composition comprising a herbicidally effective amount of a benzodisultam according to claim 1 in admixture with a diluent.

6. A method of combating mono- and di-cotyledenous plants which comprises applying to such plants a herbicidally effective amount of a benzodisultam according to claim 1.

7. The method according to claim 6, wherein the benzodisultam is

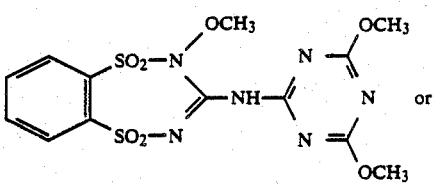 or

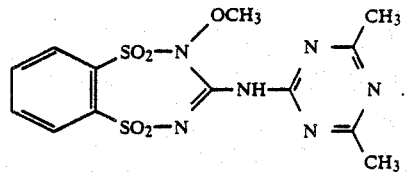

* * * * *